(12) United States Patent
Thiessies

(10) Patent No.: US 11,446,427 B2
(45) Date of Patent: Sep. 20, 2022

(54) IRRIGATION SYSTEM

(71) Applicant: UTK Solution GmbH, Luedenscheid (DE)

(72) Inventor: Olaf Thiessies, Luedenscheid (DE)

(73) Assignee: UTK Solution GmbH, Luedenscheid (DE)

(*) Notice: Subject to any disclaimer, the term of this patent is extended or adjusted under 35 U.S.C. 154(b) by 308 days.

(21) Appl. No.: 16/762,614

(22) PCT Filed: Nov. 8, 2018

(86) PCT No.: PCT/EP2018/080622
§ 371 (c)(1),
(2) Date: May 8, 2020

(87) PCT Pub. No.: WO2019/092109
PCT Pub. Date: May 16, 2019

(65) Prior Publication Data
US 2020/0345925 A1    Nov. 5, 2020

(30) Foreign Application Priority Data

Nov. 10, 2017    (DE) .................... 20 2017 106 855.2

(51) Int. Cl.
*A61M 3/00*    (2006.01)
*A61M 3/02*    (2006.01)

(52) U.S. Cl.
CPC ........ *A61M 3/0258* (2013.01); *A61M 3/0275* (2013.01); *A61M 2205/8206* (2013.01); *A61M 2205/8237* (2013.01); *A61M 2210/02* (2013.01)

(58) Field of Classification Search
CPC .. A61M 2205/8206; A61M 2205/8237; A61M 2210/02

USPC .............. 604/310, 151, 152, 153, 131, 130; 601/161

See application file for complete search history.

(56) References Cited

U.S. PATENT DOCUMENTS

| | | | |
|---|---|---|---|
| 5,197,460 A * | 3/1993 | Ito .......................... | A61C 17/02 601/162 |
| 5,746,721 A | 5/1998 | Pasch et al. | |
| 5,776,153 A * | 7/1998 | Rees ...................... | A61B 17/22 606/159 |
| 5,882,319 A * | 3/1999 | Olson ................ | A61H 33/6057 601/161 |
| 2003/0036723 A1 | 2/2003 | Henniges et al. | |
| 2005/0171504 A1* | 8/2005 | Miller ................ | A61B 17/1671 604/506 |
| 2005/0203439 A1* | 9/2005 | Heske .................... | A61B 90/03 606/167 |

(Continued)

FOREIGN PATENT DOCUMENTS

DE       696 02 175 T2    9/1999
DE  10 2011 018 708 A1   10/2012

OTHER PUBLICATIONS

International Search Report in PCT/EP2018/080622, dated Feb. 27, 2019.

*Primary Examiner* — Andrew J Mensh
(74) *Attorney, Agent, or Firm* — Collard & Roe, P.C.

(57) ABSTRACT

An irrigation system includes a housing on which a trigger is movably mounted, a motor, an accumulator, a pump and a gearing arranged inside the housing. At least the motor and the accumulator are mounted in a drive unit which can be replaced.

8 Claims, 14 Drawing Sheets

(56) References Cited

U.S. PATENT DOCUMENTS

Figure 1:
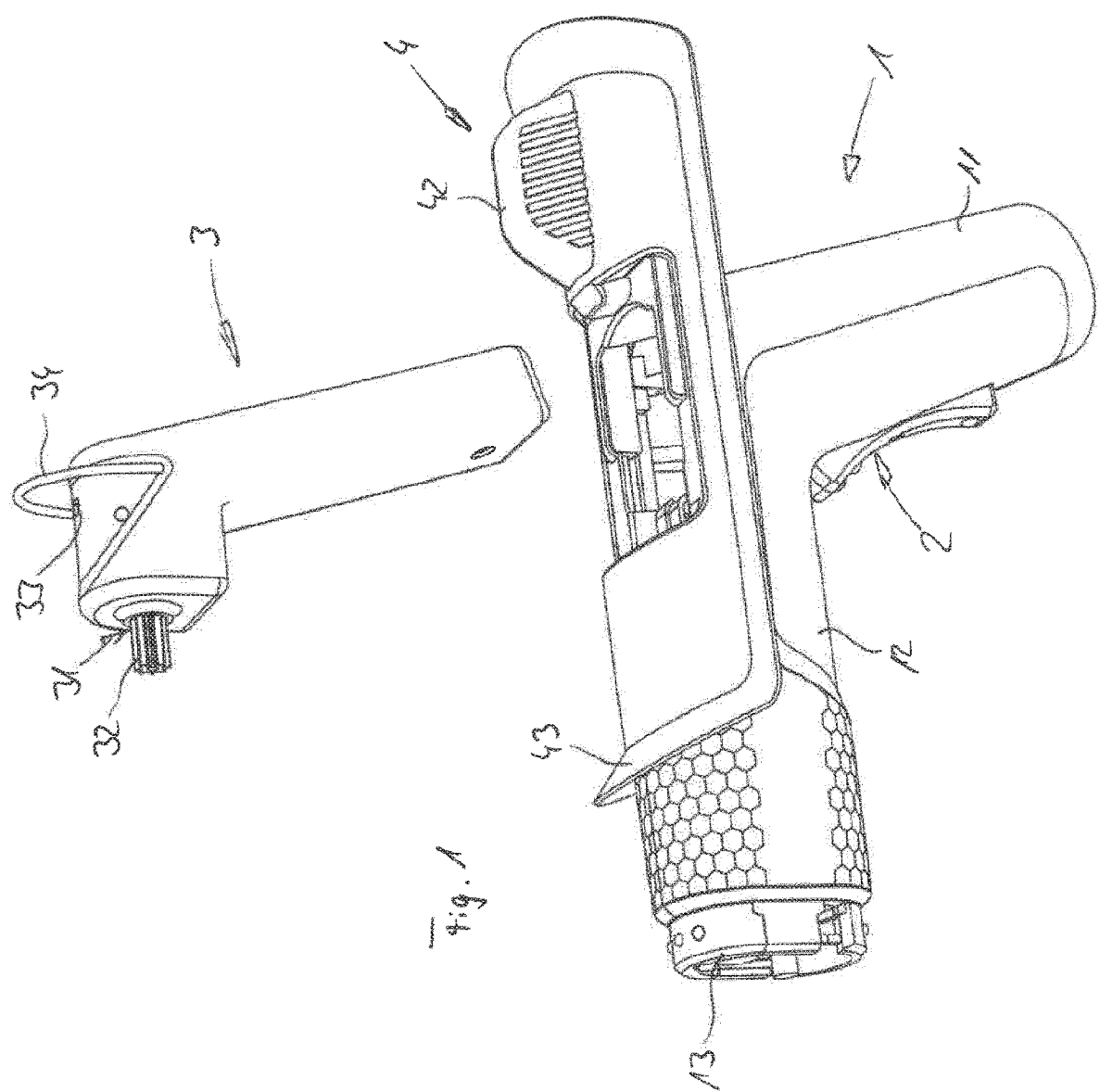

| | | | |
|---|---|---|---|
| 2009/0192443 A1* | 7/2009 | Collins, Jr. | A61M 15/008 239/338 |
| 2013/0144211 A1 | 6/2013 | Vogt et al. | |
| 2015/0182685 A1 | 7/2015 | Henniges et al. | |
| 2017/0119939 A1 | 5/2017 | Doerr et al. | |

* cited by examiner

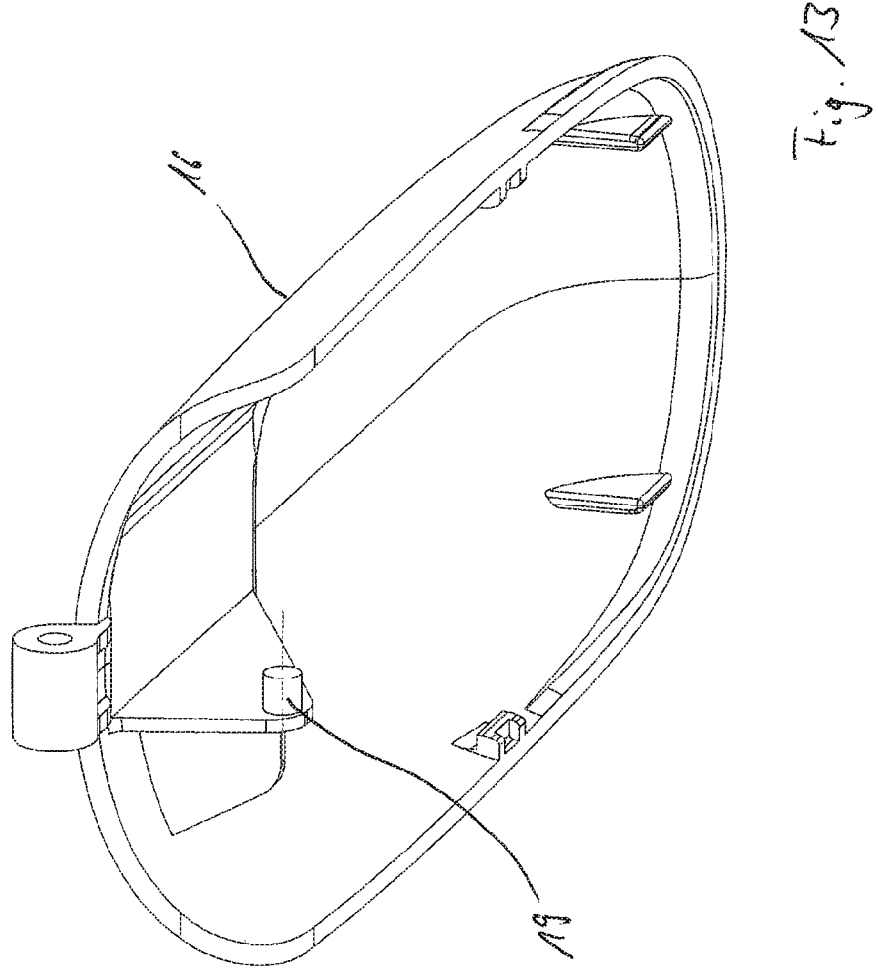

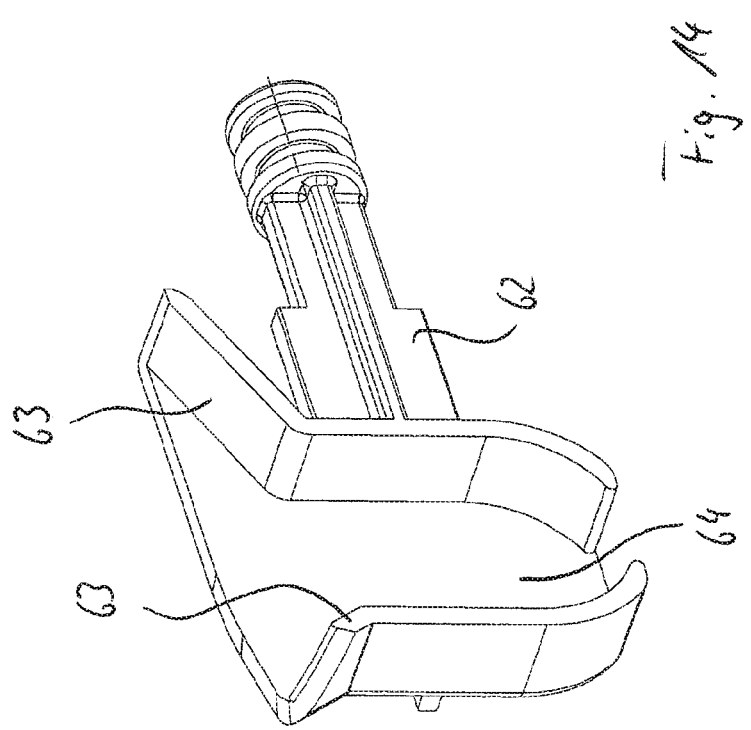

ant application is the National Stage of PCT/EP2018/080622 filed on Nov. 8, 2018, which claims priority under 35 U.S.C. § 119 of German Application No. 20 2017 106 855.2 filed on Nov. 10, 2017, the disclosure of which is incorporated by reference. The international application under PCT article 21(2) was not published in English.

IRRIGATION SYSTEM

CROSS REFERENCE TO RELATED APPLICATIONS

This application is the National Stage of PCT/EP2018/080622 filed on Nov. 8, 2018, which claims priority under 35 U.S.C. § 119 of German Application No. 20 2017 106 855.2 filed on Nov. 10, 2017, the disclosure of which is incorporated by reference. The international application under PCT article 21(2) was not published in English.

The invention relates to an irrigation system comprising a housing on which a trigger is movably mounted, wherein a motor, a rechargeable battery, a pump, and a gear mechanism are arranged in the housing.

Irrigation systems serve to flush out residues that occur in the case of an operation on bone, such as, for example, insertion of an artificial joint, during the operation, so as to prevent complications after the operation and to accelerate healing, particularly since residues impair the durability of the artificial bone and can lead to infections in the region of the bone. In this regard, irrigation is to take place in thorough but simultaneously gentle manner.

A pulsing jet of a liquid is generated by means of the irrigation system. The liquid is generally sterile water or an aqueous solution that also contains pharmaceutically active substances. The irrigation water with the residues is drawn away by the irrigation system, by way of a second channel.

Irrigation systems comprise a pump, which is used to generate the pulsating liquid jet and for conveying the liquid. A drive module is connected with the irrigation system before use and serves to drive the pump.

The known irrigation systems are driven either by electric motors or by means of compressed-air motors. A disadvantage of irrigation systems driven with compressed air is that the motor must be supplied with compressed air or with a compressed gas. It is true that a compressed-air supply is generally present in operating rooms; however, the compressed-air motor must either be connected with a compressed-gas line, thereby impairing its handling, or must comprise a compressor with electrical lines or a compressed-gas cartridge, thereby making the structure of the systems complicated (cf., for example, DE 10 2011 018 708 A1).

An irrigation system is known from US 2003/036 723 A1, in which the pump is driven by an electric motor by way of a gear mechanism. The energy for the motor is fed in by way of a power cable, thereby also restricting its handling. To avoid this disadvantage, battery-operated irrigation systems are known (cf., for example, DE 696 02 175 T2).

It is true that the known irrigation systems accomplish their task. However, the irrigation systems are usually conceived as disposable articles due to hygiene requirements. Consequently, the systems are disposed of after use, specifically including all their components, in particular the drive and the electrical energy supply. This is not justifiable, neither with regard to the aspect of saving resources nor with regard to the aspect of saving costs.

Against this background, the invention is based on the task of creating an irrigation system in which the energy supply and the components relating to drive are reusable. According to the invention, this task is accomplished in that at least the motor and the rechargeable battery are built into a drive unit that can be interchanged.

With the invention, an irrigation system is created in which the energy supply and the components relating to drive can be reused. By means of combining motor and rechargeable battery into a drive unit that can be interchanged, the possibility exists of removing the drive unit from the housing after use of the irrigation system and inserting it into the housing of a different irrigation system. Consequently, the drive unit can be inserted into different housings for a plurality of irrigation procedures. Therefore the irrigation system according to the invention makes available a resource-saving and thereby environmentally friendly and cost-advantageous solution.

In a further development of the invention, the drive unit is provided with electrical contacts. The electrical contacts allow a connection with the other individual parts installed in the housing, in particular contacting with the trigger, so as to trigger a signal in the drive unit when the trigger is activated, which signal activates the motor and thereby triggers an irrigation procedure.

Preferably, the drive unit is protected against splashing water or is liquid-tight. The configuration of being protected against splashing water or being liquid-tight leads, for one thing, to great operational reliability, and for another thing, thereby the possibility exists of sterilizing the drive unit as needed.

In an advantageous embodiment, a shaft projects out of the drive unit, which shaft is provided with a gearwheel at its free end. Drive of the pump takes place by way of the shaft having the gearwheel, with the interposition of a further gearwheel. In this way, a solution that is simple in terms of design is brought about, which simultaneously ensures great operational reliability.

In another embodiment of the invention, the drive unit has a circular eccentric gearwheel, on which a cam is arranged. By means of the cam, the rotating movement of the eccentric gear wheel can be converted into an axial movement of the tappet of the pump, and thereby a type of drive that is simple in terms of design and simultaneously very robust is created.

It is advantageous if the drive unit is provided with a handle. The handle allows easy removal and installation of the drive unit from and into the housing.

It is extremely advantageous if the rechargeable battery is rechargeable. As the result of the rechargeability of the rechargeable battery, an almost unlimited period of use exists, since after use, the drive unit having the rechargeable battery can be set into a charging station or connected with such a station, so that disposal in the event of complete emptying of the rechargeable battery, as it is known for non-rechargeable rechargeable batteries (batteries), is avoided.

In a further embodiment of the invention, the drive unit is provided with a display at its head-side end. Using the display, the user can be informed about the charging status of the rechargeable battery.

Figure 2:
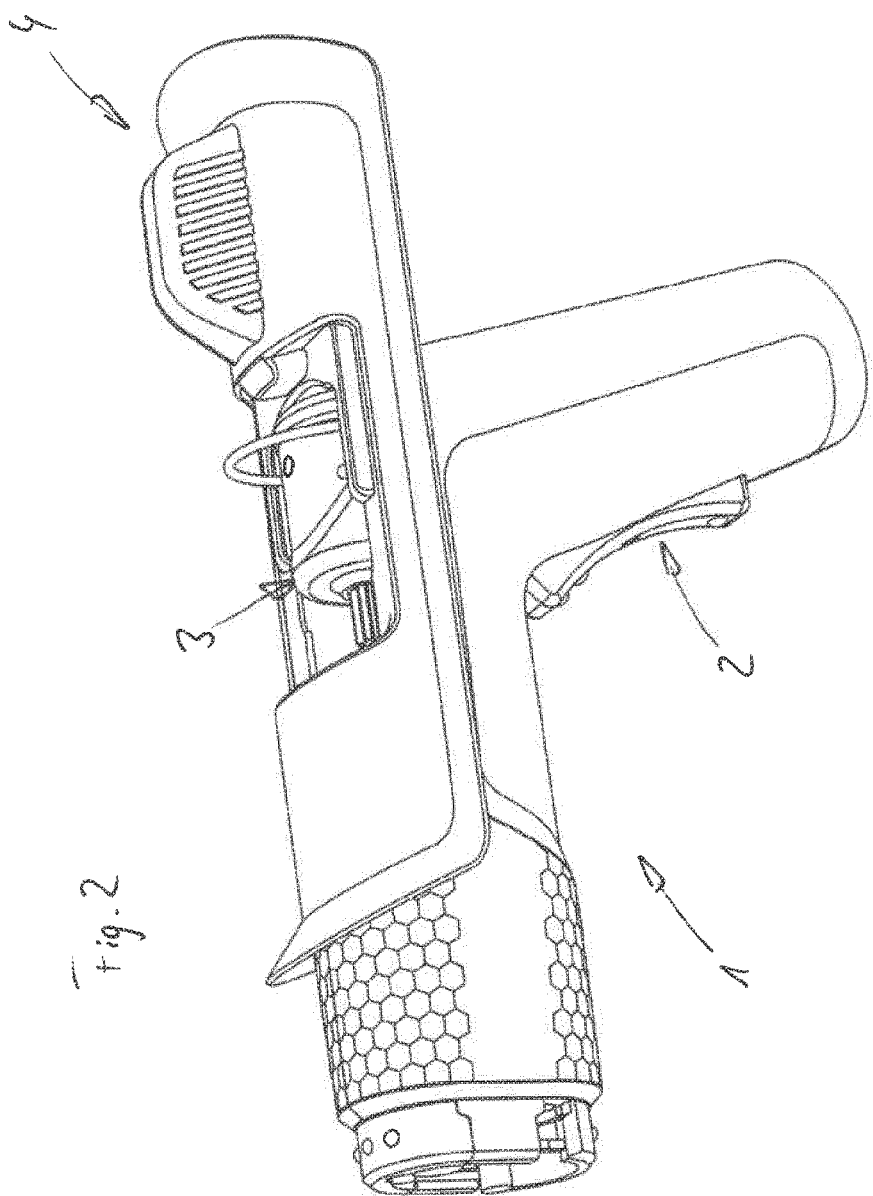
Figure 3:
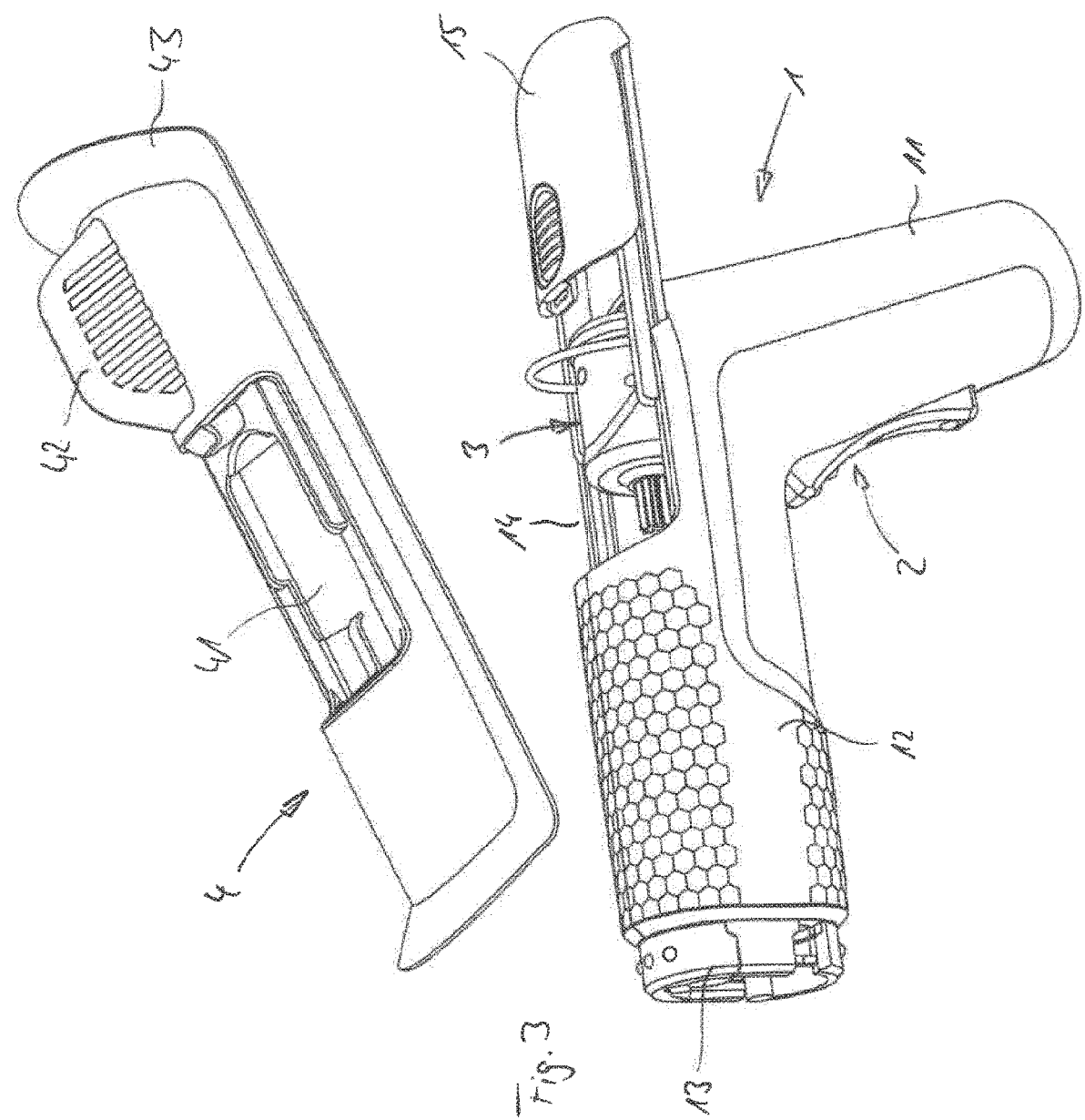
Figure 4:
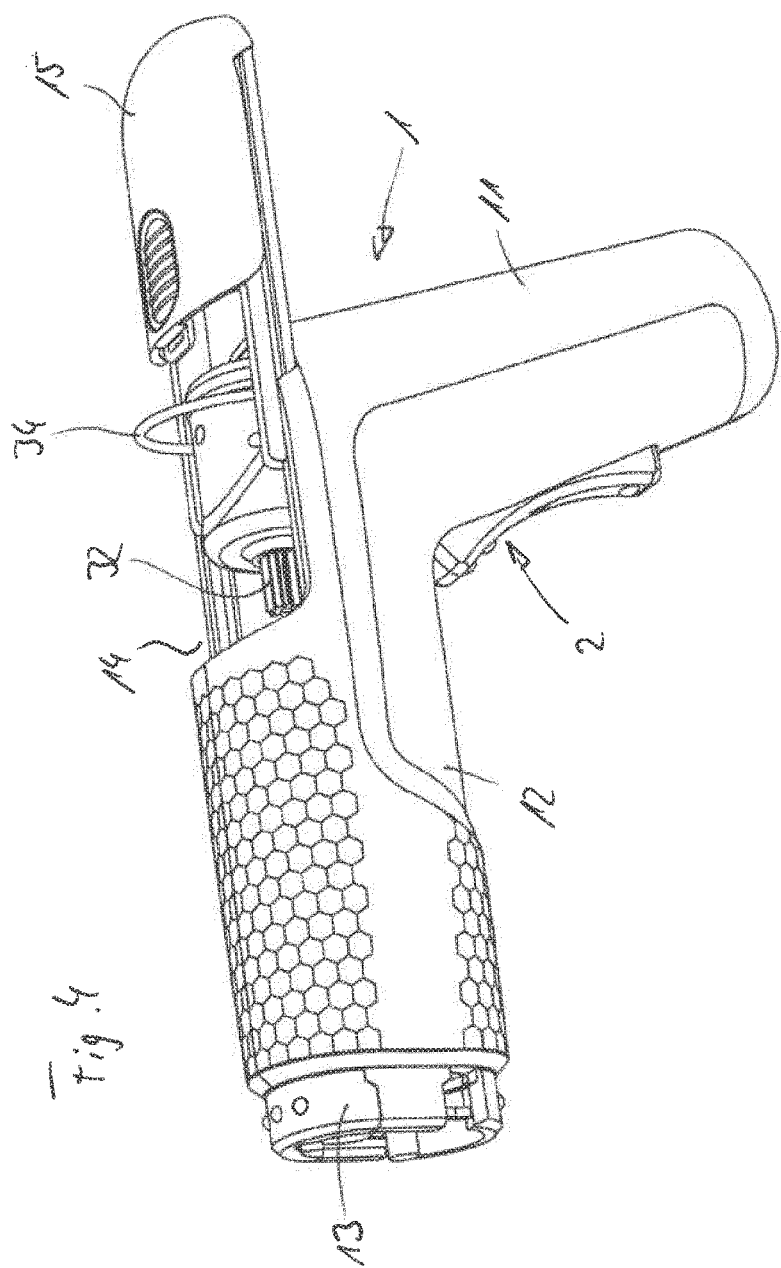
Figure 5:
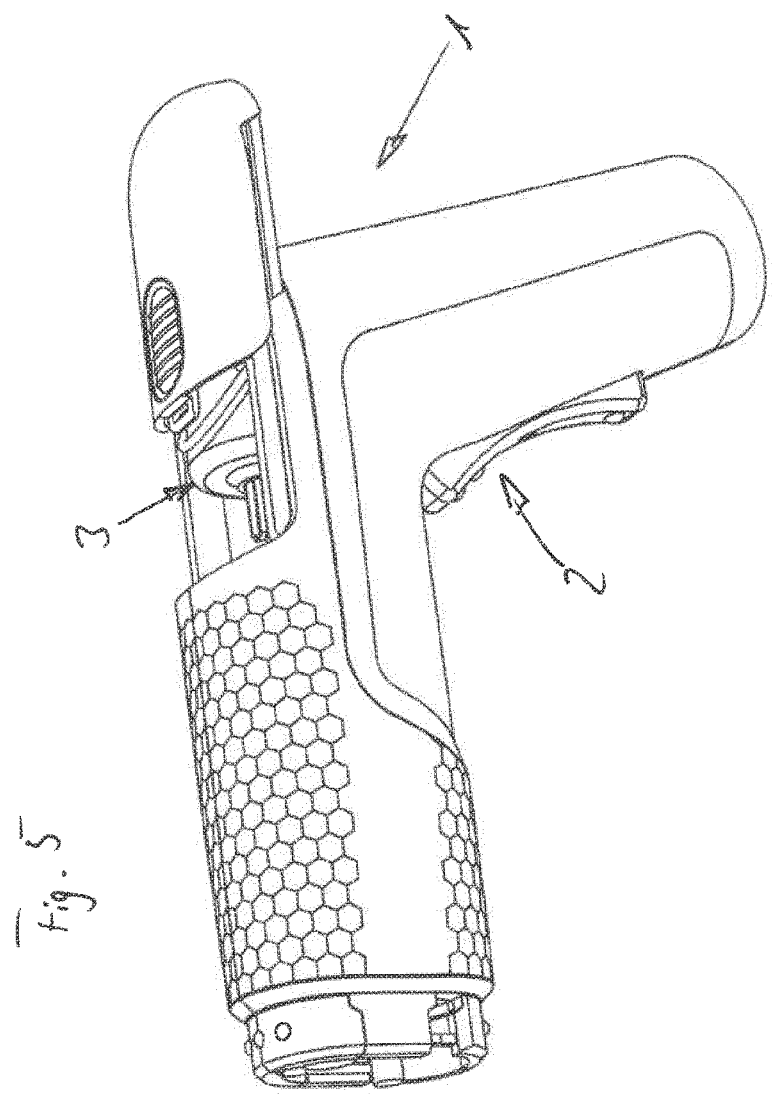
Figure 6:
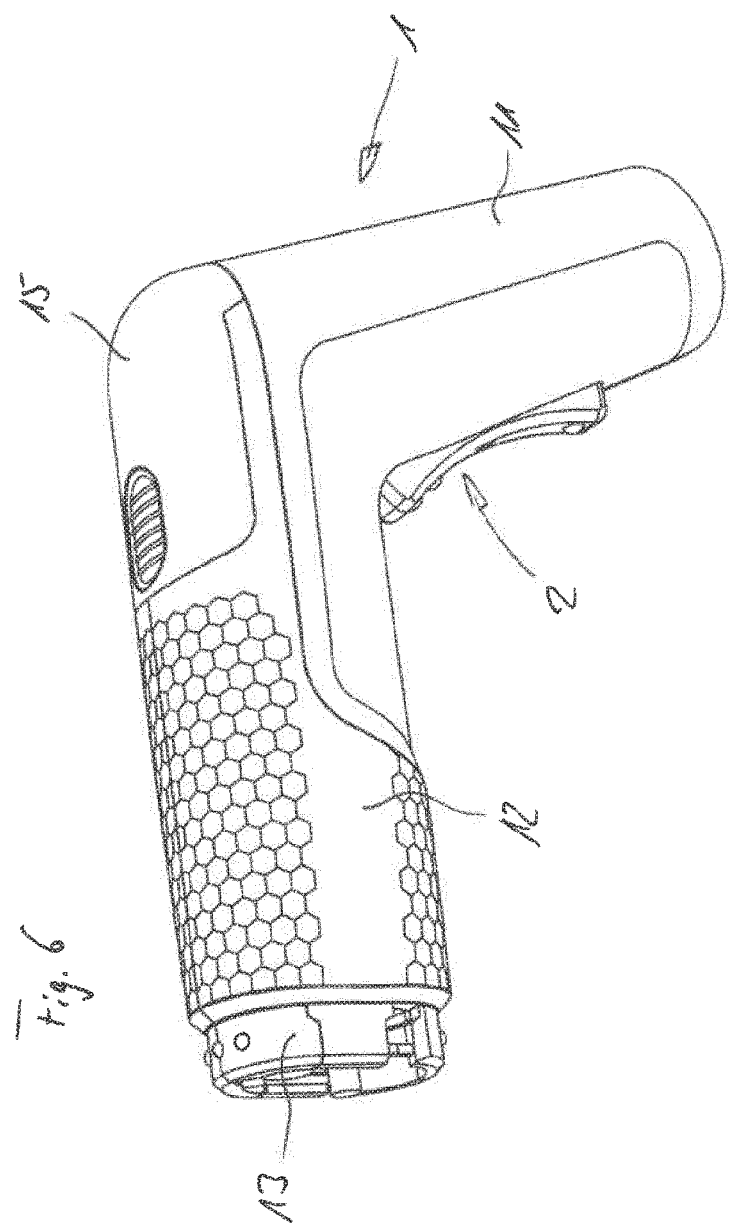
Figure 7:
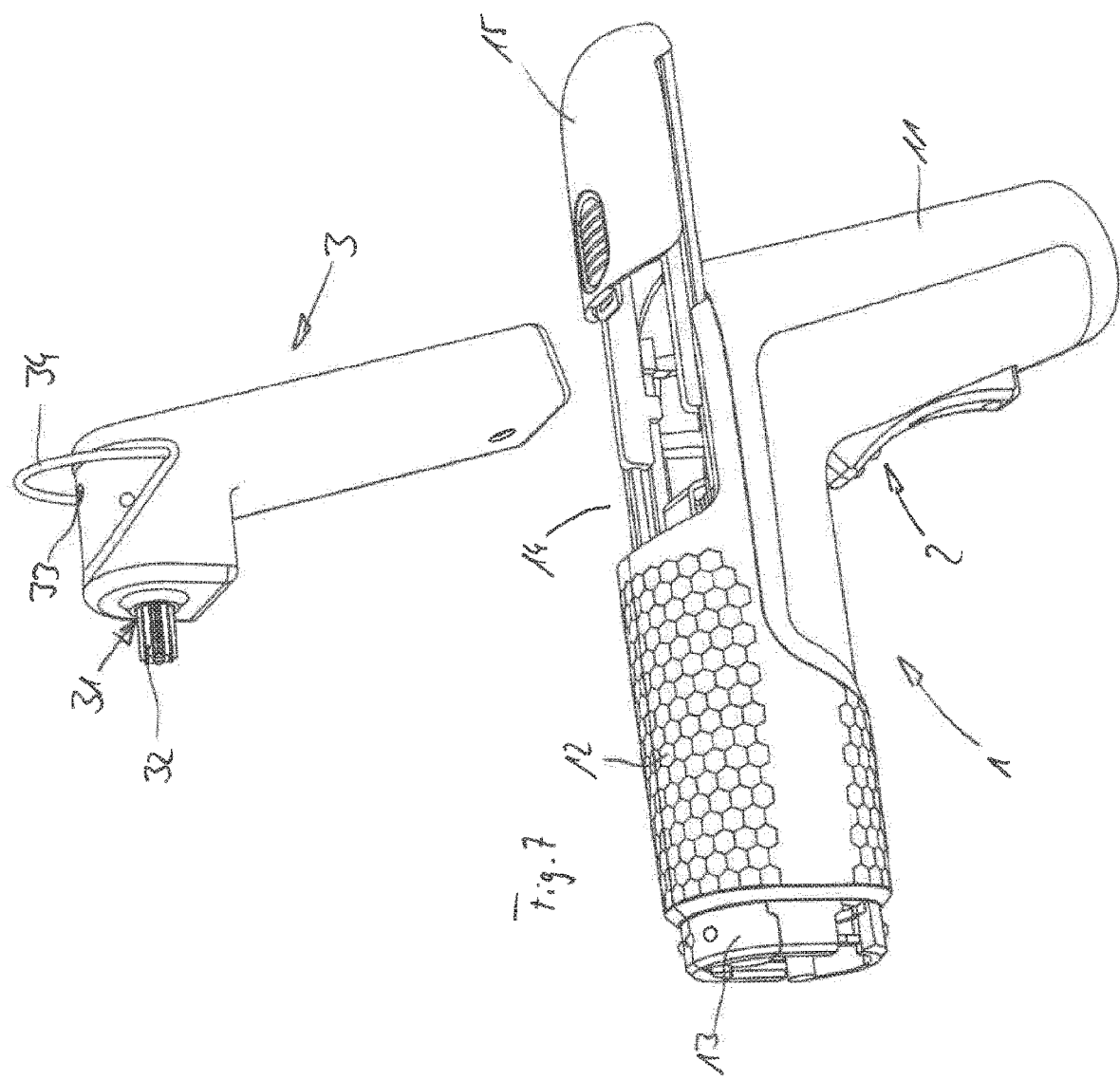
Figure 8:
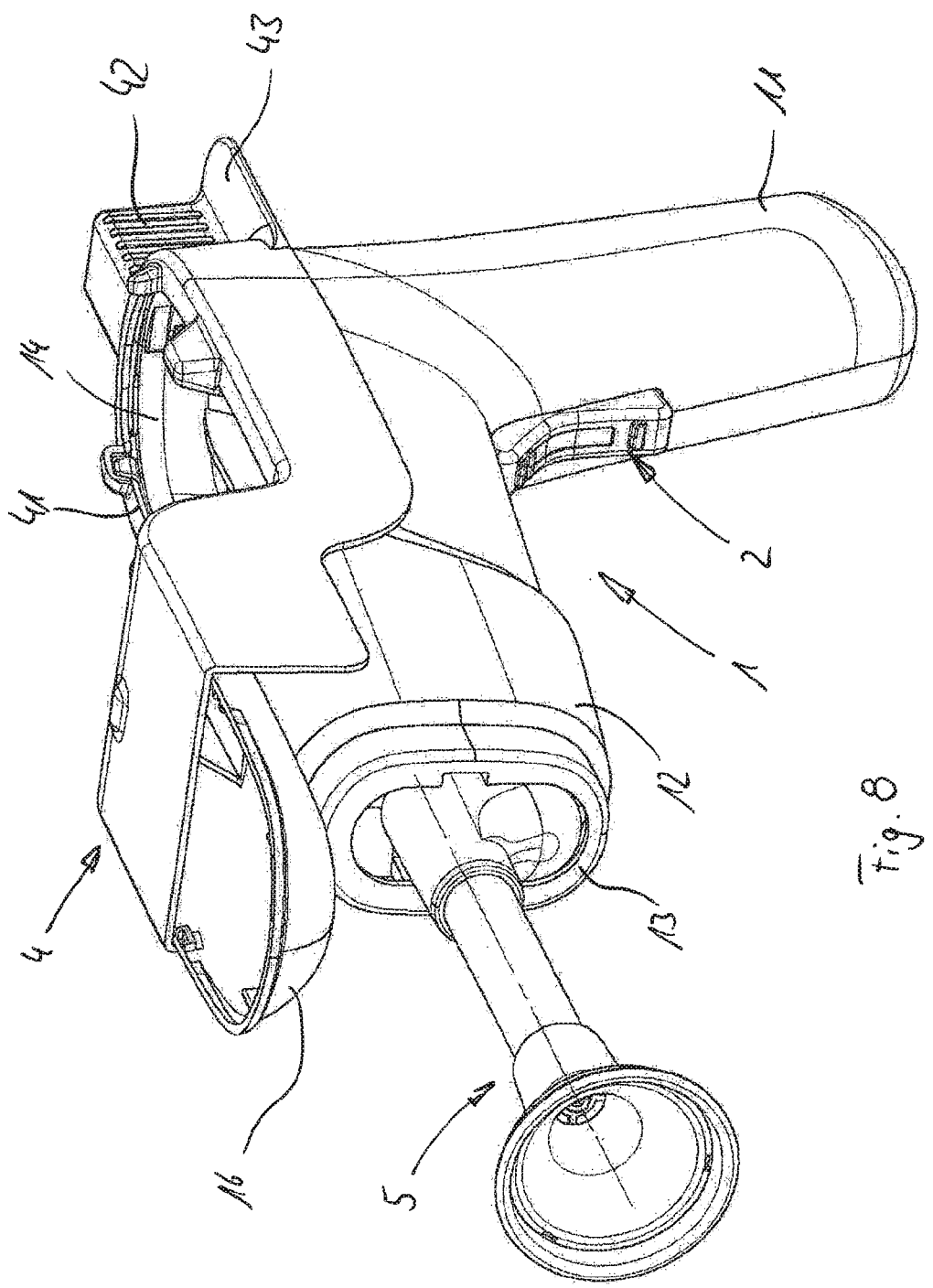
Figure 9:
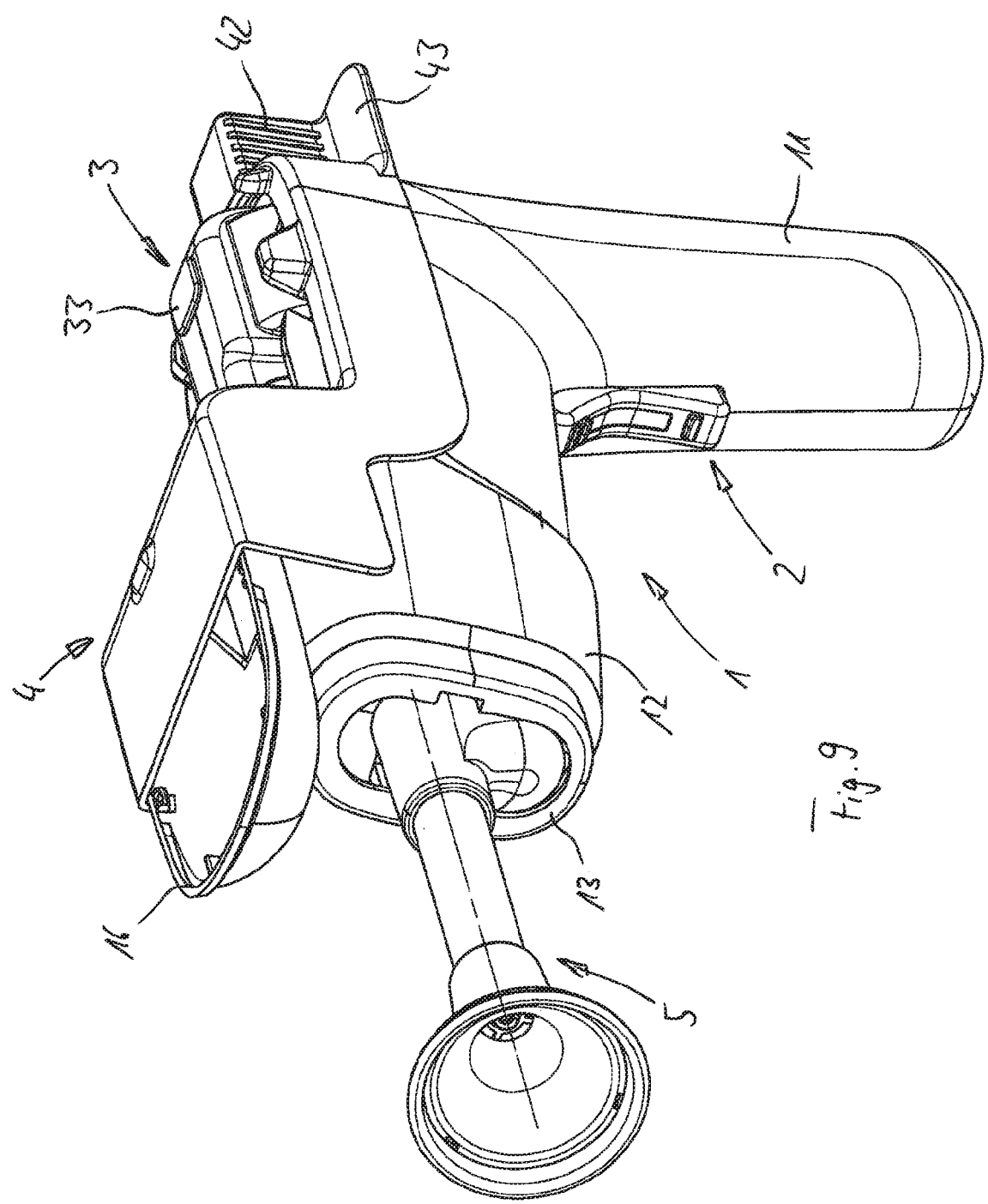
Figure 10:
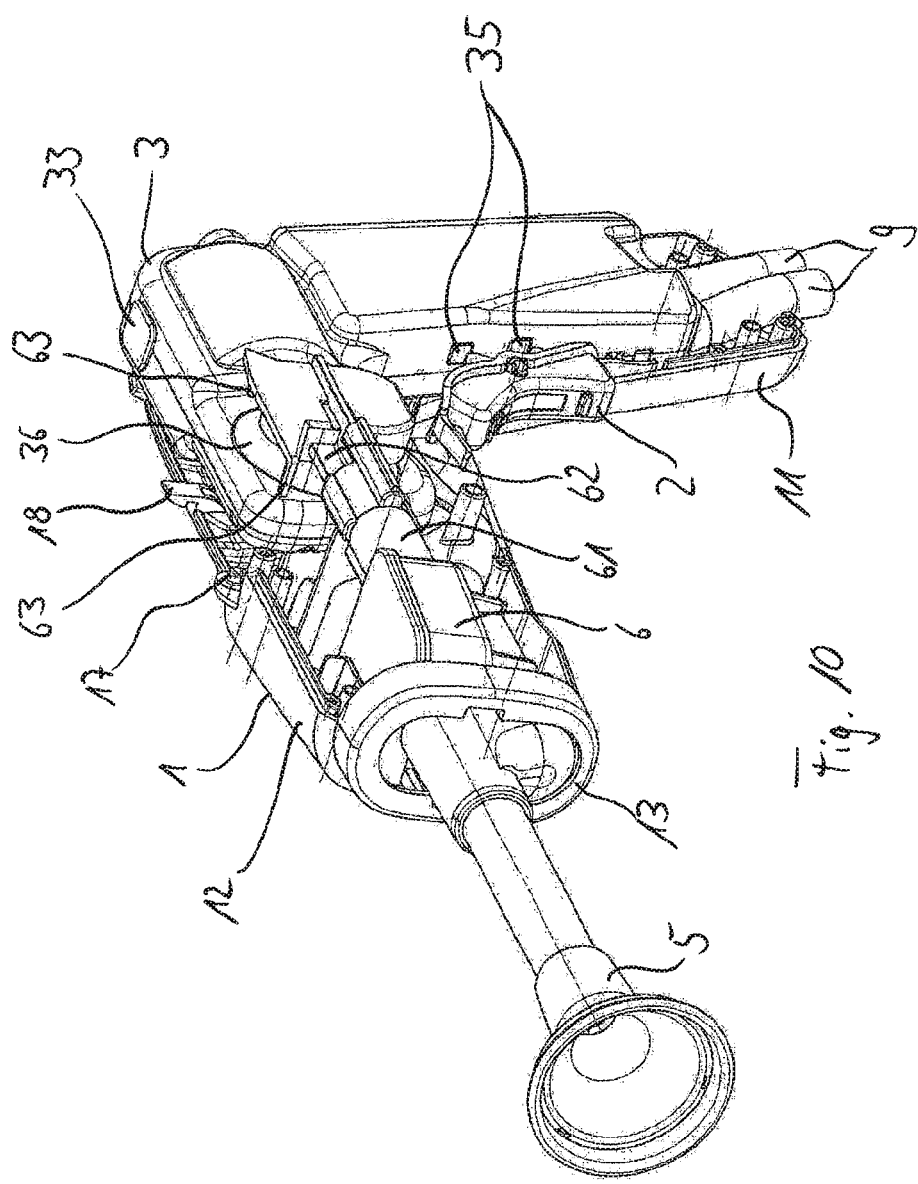
Figure 11:
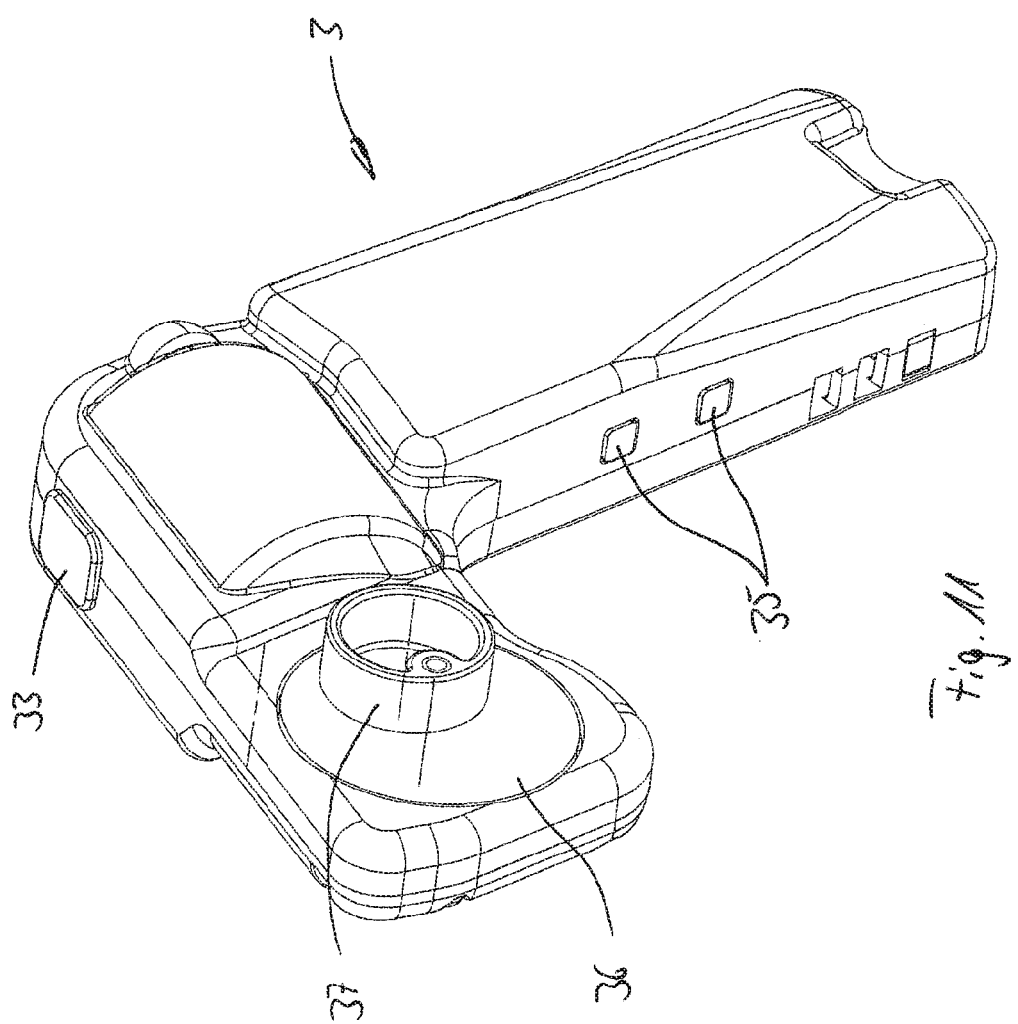
Figure 12:
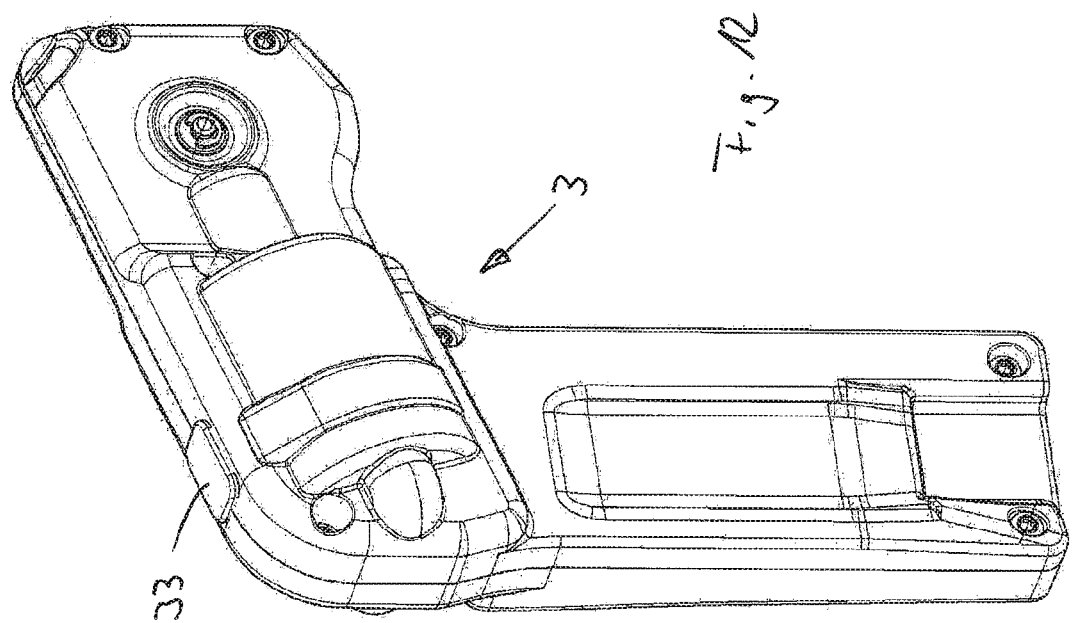

Other further developments and embodiments of the invention are indicated in the other dependent claims. Exemplary embodiments of the invention are shown in the drawings and will be described in detail below. The drawing shows:

FIG. 1 the perspective representation of an irrigation system having an introduction aid and a drive unit shown in an exploded view;

FIG. 2 the perspective representation of the irrigation system shown in FIG. 1, with introduction aid and inserted drive unit;

FIG. 3 the perspective representation of the irrigation system shown in FIG. 1, with the introduction aid removed and the slide cover open;

FIG. 4 the perspective representation of the irrigation system, with the slide flap completely open;

FIG. 5 the irrigation system shown in FIG. 4, with the slide flap partly closed;

FIG. 6 the irrigation system shown in FIG. 4, with the slide flap closed;

FIG. 7 the irrigation system shown in FIG. 4, with the drive unit shown in an exploded view;

FIG. 8 the perspective representation of an irrigation system in a different embodiment, with the cover open, the introduction aid, and the spray nozzle, without a drive unit;

FIG. 9 the perspective representation of the irrigation system shown in FIG. 8, with the cover open, the introduction aid, and the spray nozzle, with the drive unit inserted;

FIG. 10 the perspective representation of the irrigation system shown in FIG. 8, with the housing partly shown in section, and the drive unit inserted;

FIG. 11 the perspective representation of a drive unit;

FIG. 12 the drive unit shown in FIG. 11 from a different perspective;

FIG. 13 the perspective representation of a flap cover;

FIG. 14 the perspective representation of a tappet.

The irrigation system according to the invention comprises a housing 1 made of plastic, which is formed by a grip part 11 and a functional part 12. A trigger 2 is movably mounted on the housing 1, wherein the trigger 2 is arranged in the grip part 11. The trigger 2 is formed in the manner of a tilt lever. A holder 13 is provided on the end of the functional part 12 that faces away from the grip part 11, which holder serves to connect attachments. The attachments can be formed in known manner and provided with a splash guard at their free end. Such an attachment is shown in FIGS. 8 to 9 and indicated as "5." In general, the attachments are configured in such a manner that two hose-like lines are provided, one of which conveys the irrigation solution in the direction toward the wound to be irrigated, and the other of which suctions the irrigation solution, together with the contaminants, out of the wound. The attachments can be configured for cleaning bone, soft tissue, or for flushing. Also, brush attachments or the like can be used.

The housing 1 is provided with an opening 14, which can be closed off, in the exemplary embodiment according to FIGS. 1 to 7, by means of a slide flap 15. In the exemplary embodiment according to FIGS. 8 to 14, in contrast, the opening can be closed off by means of a flap cover 16, which can be pivoted about the axis of hinges 17 provided on the housing 1 (cf. FIG. 9). In the closed state, the flap cover 16 is locked in place by means of engagement projections 18 provided on the housing 1. Furthermore, a hold-down mechanism 19 is formed on the flap cover 16.

Preferably, the slide flap 15 and the flap cover 16 are produced from transparent material. In the housing 1, a shaft is formed in the grip part 11, which shaft holds a drive unit 3. In the exemplary embodiments, a motor for operation of the irrigation system and a rechargeable battery are built into the drive unit 3. In the exemplary embodiment, the rechargeable battery is rechargeable.

The drive unit 3 is provided with electrical contacts 35, which correspond with electrical contacts in the housing 1. In this manner, a connection is created between the drive unit 3 and the trigger 2, so that activation of the trigger 2 starts the motor in the drive unit 3. At the same time, the electrical contacts serve for charging the rechargeable battery in the drive unit 3, in that the drive unit 3 is positioned in a charging station or connected with a charging device.

The drive unit 3 is configured to be liquid-tight. At its head-side end, a shaft 31 projects out of the drive unit 3 in the exemplary embodiment according to FIGS. 1 to 7, which shaft is provided with a gearwheel 32 at its free end. The gearwheel 32 is preferably produced from high-performance plastic. In the exemplary embodiment according to FIGS. 8 to 14, in contrast, the drive unit 3 has a circular eccentric gearwheel 36 at the side, on which a cam 37 is arranged. The eccentric gearwheel 36 is provided with a freewheel.

Furthermore, the drive unit 3 is provided with a display 33 at its head-side end, which displays the charging status of the rechargeable battery. The display 33 is arranged below a window, so as to guarantee the embodiment of the drive unit 3 as protected against splashing water or being liquid-tight. The drive unit 3 is furthermore provided with a handle 34, which consists of a pivoting bracket in the exemplary embodiment according to FIGS. 1 to 7. The pivoting bracket has a shape that essentially corresponds to the shape of the head-side end of the drive unit 3. In the non-used state, the handle 34 can therefore be folded in, in such a manner that it lies against the contour of the drive unit 3.

Heat sensors are provided in the drive unit 3, on a circuit board, which sensors monitor the operating temperature of the drive unit 3, in particular in the region of the motor. They stand in connection with the display 33. If the sensors measure an overly high operating temperature, a signal is sent to the display 33. The display 33 thereupon signals the faulty operating state to the user. A current monitor and charging electronics can also be arranged on the circuit board.

The drive unit 3 can be locked in place in the housing 1 by means of what is called a push/pull locking mechanism. This means that the drive unit 3 locks in place when it is inserted into the housing 1 from above, through the opening 14, when it reaches its functional position. In the closed state of the flap cover 16, the hold-down mechanism 19 holds the drive unit 3 in its functional position, in this regard. To unlock the drive unit 3, all that is required after the slide flap 15 or the flap cover 16 is opened is to exert pressure on the drive unit 3 from above, and thereby the drive unit 3 is released from its locked position.

A pump 6 is arranged in the housing 1. The pump 6 is preferably configured in two parts and provided with a tappet 62, which is guided in a guide 61. The pump 6 interacts with a gear mechanism that is also arranged within the housing, wherein the connection of the pump 6 with the drive unit 3 is referred to as a gear mechanism. The gear mechanism in turn stands in contact with the gearwheel 32 in accordance with the exemplary embodiment according to FIGS. 1 to 7. In the exemplary embodiment according to FIGS. 8 to 14, the gear mechanism is formed by the cam 37 and a holder 64, in which the cam 37 is positioned in the installed state. The pump 6 can be a vacuum pump, a membrane pump or the like. The pump 6 is connected with two hoses 9, which are provided in the housing 1 and exit from the grip part 21 on the end facing away from the functional part 22 (cf. FIG. 10). The hoses 9 stand in connection, on the one side, with a supply container for the irrigation liquid, on the other side with a collection container for the liquid suctioned out of the wound. The hoses 9 run within the housing 1, under a cover—not shown—so as to prevent contact with the drive unit 3.

The irrigation system according to the invention is delivered with an introduction aid 4. The introduction aid 4 is clamped onto the housing 1 and can be removed. As can be seen in FIGS. 1 and 2 as well as 8 and 9, the introduction aid 4 covers the top side of the housing 1 in the installed state. It has a recess 41, the size and shape of which essentially correspond to that of the opening 14 in the housing 1. A grip 42 is formed adjacent to the recess 41. Furthermore, the introduction aid 4 has an edge 43, which is structured to be circumferential in the exemplary embodiment according to FIGS. 1 to 7.

In the case of the irrigation system according to the invention, the motor and the rechargeable battery are built into the drive unit 3. The drive unit 3 is interchangeable, as can be seen, in particular, in FIGS. 1 and 7. For inserting the drive unit 3, the slide flap 25 is displaced in the direction facing away from the holder 23, as is shown in FIG. 4; in the exemplary embodiment according to FIG. 9, the flap cover 16 is flipped open. At the same time, the introduction aid 4 is affixed to the housing 1. As is shown in FIG. 1, for example, the operator can insert the drive unit 3 into the housing 1 from above, in that he/she introduces the drive unit 3 through the recess 41 and the opening 14 along the shaft configured in the grip part 11. During introduction, in the exemplary embodiment according to FIGS. 8 to 13, the cam 37 comes into contact with run-in bevels 63, which results in a rotation of the eccentric gearwheel 36 due to the freewheel, and brings the cam 37 into a position in the holder 64 that is predetermined by the design. As a result, the cam 37 automatically assumes the position required for operation of the pump 6 in the functional position of the drive unit 3.

Once the drive unit 3 has been introduced into the housing 1, it assumes the position shown in FIGS. 2 and 9. The introduction aid 4 is then removed from the housing 1 (FIG. 3). In this assumed working position, the contacts on the drive unit 3 enter into contact with the contacts in the housing 1. At the same time, in this position the gearwheel 32 or the cam 37 is in the position suitable for operation of the pump 6. Using the cam 37 arranged on the eccentric gearwheel 36, which rotates during operation, the rotational movement of the drive is converted to an axial movement of the tappet of the pump 6.

After the handle 34 is folded in, the slide flap 15 is displaced in the direction of the holder 13 in the exemplary embodiment according to FIGS. 1 to 7, until it has reached its closing position, as shown in FIG. 6. In the exemplary embodiment according to FIGS. 8 to 14, the flap cover 16 is flipped about the axis formed by the hinges 17, until the flap cover 16 engages with the engagement projections 18. Since the slide flap 15 or the flap cover 16 is configured to be transparent, the display 33 of the drive unit 3 can be seen even when the slide flap 15 or the flap cover 16 is closed. After the irrigation system is connected with the liquid container and collection container, and after the respectively desired attachments have been inserted into the holder 13, the irrigation system can be put into operation by activation of the trigger 2. This is done in a manner known from other irrigation systems.

After use of the irrigation system according to the invention, the drive unit 3 can be removed from the housing 1 by means of opening the slide flap 15 or the flap cover 16. For this purpose, first pressure is exerted on the drive unit 3 from above, so as to unlock it. Then the handle 34 can be flipped upward, so that the user can grasp it and remove the drive unit 3 from the housing 1. After removal of the drive unit 3, as it is shown in FIG. 7, for example, the housing 1, which consists only of plastic, can be disposed of, together with the components arranged in it. The drive unit 3 itself can be brought to a charging station, so as to supply the rechargeable rechargeable battery with current.

Due to the configuration of the drive unit 3 as being protected against splashing water or being liquid-tight, the possibility fundamentally exists of cleaning and/or sterilizing the drive unit 3 with the components arranged in it. As a result, all demands regarding hygiene in the operation area are met. There are no hygiene reservations in this regard, since during insertion of the drive unit 3, only contact with the introduction aid 4 can come about, but the latter is removed after introduction. Consequently, the housing 1 remains sterile on the outside, even if a non-sterile drive unit 3 is introduced.

Because of the manifold usability of the drive unit 3, disposal of complete irrigation systems including drive and power supply, as known from the state of the art, is prevented, and this makes a significant contribution to environmental protection and to reduction of costs. Because the housing 1, including trigger 2, pump 6, and gear mechanism, consists exclusively of plastic, the possibility of very easy recycling also exists, since it is possible to eliminate prior separation of individual components made of different materials, in particular of metals.

Furthermore, because of the plastic selected for the housing 1, reliable and, at the same time, fatigue-free handling is also made possible. Furthermore, the irrigation system according to the invention is easy to handle because of its ergonomic design, and therefore offers the operator convenient and fatigue-free operation.

The invention claimed is:

1. An irrigation system comprising a housing (1) on which a trigger (2) is movably mounted,
    wherein a motor, a rechargeable battery, a pump (6), and a gear mechanism are arranged in the housing (1),
    wherein at least the motor and the rechargeable battery are built into a drive unit (3) that is configured to be interchanged,
    wherein the drive unit (3) is provided with a handle (34) and is configured to be inserted into the housing (1) from above, through an opening (14), and
    wherein the opening is configured to be closed off with a slide flap (15) or a flap cover (16), which comprises transparent plastic, through which a display (33) provided at the head-side end of the drive unit (3) is configured to be seen while the side flap (15) or flap cover (16) is in a closed state.

2. The irrigation system according to claim 1, wherein the drive unit (3) is provided with electrical contacts.

3. The irrigation system according to claim 1, wherein the drive unit (3) is protected against splashing water.

4. The irrigation system according to claim 1, wherein the drive unit (3) is liquid-tight.

5. The irrigation system according to claim 1, wherein a shaft (31) projects out of the drive unit (3), which shaft is provided with a gearwheel (32) at its free end.

6. The irrigation system according to claim 1, wherein the drive unit (3) has a circular eccentric gearwheel (36), on which a cam (37) is formed.

7. The irrigation system according to claim 1, wherein an introduction aid (4) is provided.

8. The irrigation system according to claim 1, wherein the housing (1), trigger (2), pump (6), and gear mechanism comprise plastic.

* * * * *